United States Patent [19]

Hurt

[11] 4,086,337
[45] Apr. 25, 1978

[54] O,S-DIALKYL O(S)-SULFONYLOXY(THIO)PHENYL PHOSPHOROTHIOLATES AND PHOSPHORODI(TRI)THIOATES

[75] Inventor: William S. Hurt, Collegeville, Pa.

[73] Assignee: Rohm and Haas Company, Philadelphia, Pa.

[21] Appl. No.: 696,470

[22] Filed: Jun. 16, 1976

[51] Int. Cl.$^2$ .................. C07C 143/48; A01N 9/36
[52] U.S. Cl. ................. 424/215; 260/456 P; 260/947
[58] Field of Search ............ 260/450 P, 456 P, 947; 424/225, 303, 215; 71/87

[56] References Cited

U.S. PATENT DOCUMENTS

| | | | |
|---|---|---|---|
| 3,408,382 | 10/1968 | Sirrenberg et al. | 424/303 |
| 3,419,620 | 12/1968 | Becher et al. | 260/456 P |
| 3,444,274 | 5/1969 | Schrader | 424/225 |
| 3,898,305 | 8/1975 | Beriger et al. | 424/225 |
| 3,898,334 | 8/1975 | Kishino et al. | 424/225 |
| 3,911,122 | 10/1975 | Drabek et al. | 242/225 |
| 3,961,043 | 6/1976 | Huvar | 424/225 |

Primary Examiner—James O. Thomas, Jr.
Assistant Examiner—James H. Reamer

[57] ABSTRACT

This invention relates to novel organophosphorothiolates and phosphorodi(tri)thioates of the formula:

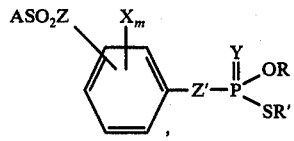

wherein

R is a $(C_1-C_4)$ alkyl group;
R' is a $(C_3-C_6)$ alkyl group;
Y is an oxygen or sulfur atom;
Z and Z' are independently oxygen or sulfur atoms, provided that Z and Z' are not simultaneously oxygen atoms;
X is a halogen atom, a $(C_1-C_5)$ alkyl group, or a $(C_1-C_5)$ alkoxy group;
m is an integer from 0 to 3; and
A is
  a. a $(C_1-C_6)$ alkyl group optionally substituted with up to three halogen atoms;
  b. a $(C_5-C_6)$ cycloalkyl group;
  c. a $(C_7-C_{11})$ aralkyl group, the aryl portion of which is optionally substituted with up to three substituents selected from the group consisting of halogen, nitro, $(C_1-C_5)$ alkyl, and $(C_1-C_5)$ alkoxy;
  d. an aryl group of the formula:

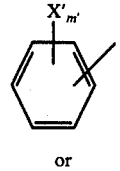

or

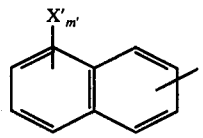

wherein

X' is a halogen atom, a nitro group, a $(C_1-C_5)$ alkyl group, or a $(C_1-C_5)$ alkoxy group; and
m' is an integer from 0 to 3;

to compositions containing them and to methods of using them to control pests.

15 Claims, No Drawings

O,S-DIALKYL O(S)-SULFONYLOXY(THIO)PHENYL PHOSPHOROTHIOLATES AND PHOSPHORODI(TRI)THIOATES

This invention relates to novel organophosphorothiolates and phosphorodi(tri)thioates having pesticidal activity, to compositions containing them, and to methods of using them to control a variety of harmful pests including acarids, insects, nematodes, and phytopathogenic fungi. In addition to possessing outstanding pesticidal activity, compounds of the present invention possess such desirable characteristics as activity against organophosphorus resistant species, residual activity, low toxicity to warm-blooded animals and low phytotoxicity for economically important plant species.

The novel compounds of this invention can be represented by the following formula:

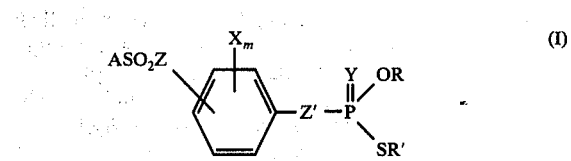 (I)

wherein
R is a $(C_1-C_4)$ alkyl group, preferably methyl or ethyl, most preferably ethyl;

R' is a $(C_3-C_6)$ alkyl group, preferably a $(C_3-C_5)$ alkyl group of the formula:

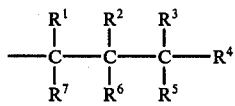

wherein $R^1-R^7$ are individually hydrogen, methyl, or ethyl;

Y is an oxygen or sulfur atom, preferably an oxygen atom;

Z is an oxygen or sulfur atom, preferably an oxygen atom;

Z' is an oxygen or sulfur atom, preferably a sulfur atom, provided that Z and Z' are not simultaneously oxygen atoms;

X is a halogen atom, preferably chlorine, a $(C_1-C_5)$ alkyl group, preferably methyl, or a $(C_1-C_5)$ alkoxy group, preferably methoxy;

m is an integer from 0 to 3; and

A is
a. a $(C_1-C_6)$ alkyl group optionally substituted with up to three halogen atoms, preferably chlorine;
b. a $(C_5-C_6)$ cycloalkyl group;
c. a $(C_7-C_{11})$ aralkyl group, preferably benzyl, the aryl portion of which is optionally substituted with up to three substituents selected from the group consisting of nitro, halogen, preferably chlorine, $(C_1-C_5)$ alkyl, preferably methyl, and $(C_1-C_5)$ alkoxy, preferably methoxy; or
d. an aryl group of the formula:

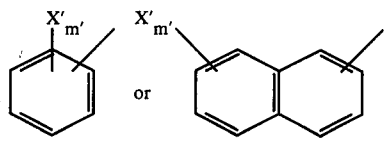

wherein X' is a halogen atom, preferably chlorine, a nitro group, a $(C_1-C_5)$ alkyl group, preferably methyl, or a $(C_1-C_5)$ alkoxy group, preferably methoxy; and m' is an integer from 0 to 3.

As used in the specification and claims, the terms "alkyl," "alkoxy" and "aralkyl" are intended to include branched chain as well as straight chain groups. Representative alkyl groups include methyl, ethyl, n-propyl, sec-butyl, isobutyl, pentyl, neopentyl, 2-methylpentyl, n-hexyl and the like. Representative alkoxy groups include methoxy, ethoxy, propoxy, sec-butoxy, pentoxy and the like. Representative aralkyl groups include benzyl, phenethyl, 3-phenyl-1-methylpropyl, naphthylmethylene, and the like.

The organophosphorothiolates and phosphorodi(tri)thioates described above can exist in their isomeric forms, wherein the $ASO_2Z$- group of Formula I is attached to the benzene ring in a position which is ortho, meta or para, preferably para, to the point of attachment of the phosphorothiolate or phosphorodi(tri)thioate group.

In a preferred embodiment of this invention, the compounds can be represented by the following formula:

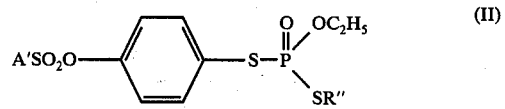 (II)

wherein R" is a n-propyl, isobutyl or sec-butyl group;

A' is a $(C_1-C_5)$ alkyl group, preferably methyl, or a phenyl group optionally substituted with up to three substituents selected from the group consisting of methyl, nitro, and chloro.

Typical compounds within the scope of this invention include the following:

O-ethyl O-[4-(methanesulfonylthio)phenyl] S-n-propyl phosphorothiolate

O-ethyl S-[4-(methanesufonylthio)phenyl] S-n-propyl phosphorodithioate

O-ethyl O-[4-(methanesulfonylthio)phenyl] S-n-propyl phosphorodithioate

O-ethyl S-[4-(methanesulfonylthio)phenyl] S-n-propyl phosphorotrithioate

S-[4-methanesulfonyloxy)phenyl] O-methyl S-n-propyl phosphorodithioate

S-sec-butyl O-ethyl S-[4-(methanesulfonyloxy)phenyl] phosphorodithioate

S-[4-(trichloromethanesulfonyloxy)phenyl] O-ethyl S-n-propyl phosphorodithioate

S-[3-(ethanesulfonyloxy)phenyl] O-ethyl S-n-propyl phosphorodithioate

O-ethyl S-[2-(isobutanesulfonyloxy)phenyl] S-n-propyl phosphorodithioate

0-[3-(n-butanesulfonylthio)phenyl] O-ethyl S-n-propyl phosphorodithioate

O-ethyl S-[2-(n-hexanesulfonyloxy)phenyl] S-isobutyl phosphorodithioate

O-[4-(cyclohexanesulfonylthio)phenyl] O-ethyl S-n-propyl phosphorothiolate

S-[3-(cyclohexanesulfonyloxy)phenyl] O-ethyl S-n-propyl phosphorodithioate

S-[4-(benzenesulfonylthio)phenyl] O-ethyl S-n-propyl phosphorodithioate

S-[4-(benzenesulfonylthio)phenyl]O-ethyl S-n-propyl phosphorotrithioate

O-[4-(benzenesulfonylthio)phenyl]O-ethyl S-n-propyl phosphorothiolate

S-[3-benzenesulfonyloxy)phenyl] S-n-butyl O-ethyl phosphorodithioate

S-[3-(benzenesulfonyloxy)phenyl] S-sec-butyl O-ethyl phosphorodithioate

S-3-(benzenesulfonyloxy)phenyl] O-ethyl S-isobutyl phosphorodithioate

S-[2-(benzenesulfonyloxy)phenyl] O-ethyl S-n-hexyl phosphorodithioate

O-ethyl S-[4-(4'-fluorobenzenesulfonyloxy)phenyl] S-isobutyl phosphorodithioate

O-ethyl S-isobutyl S-[3-(4'-nitrobenzenesulfonyloxy)phenyl]phosphorodithioate

O-ethyl S-isobutyl S-[3-(3'-nitrobenzenesulfonyloxy)phenyl]phosphorodithioate

O-ethyl S-isobutyl S-[3-(2'-nitrobenzenesulfonyloxy)phenyl]phosphorodithioate

S-[4-(4'-bromobenzenesulfonyloxy)phenyl] O-ethyl S-n-propyl phosphorodithioate

S-[4-(4'-chlorobenzenesulfonylthio)phenyl] O-ethyl S-n-propyl phosphorodithioate S-[4-(2', 4',5'-trichlorobenzenesulfonyloxy)phenyl] O-ethyl S-isobutyl phosphorodithioate O-ethyl S-n-propyl S-[4-(α-toluenesulfonyloxy)phenyl] phosphorodithioate S-[4-(3', 4'-dichloro-α-toluenesulfonyloxy)phenyl O-ethyl S-isobutyl phosphorodithioate O-ethyl S-[4-(phenethylsulfonyloxy)phenyl] S-n-propyl phosphorodithioate O-ethyl S-n-propyl O-[4-(p-toluenesulfonylthio)phenyl] phosphorothiolate S-[4-(2'-chloro-4'-methyl-α-toluenesulfonyloxy)phenyl] O-ethyl S-n-propyl phosphorodithioate S-[4-(4'-methoxybenzenesulfonyloxy)phenyl] O-methyl S-n-propyl phosphorodithioate S-[4-(4'-chloro-2'-methylbenzenesulfonyloxy)phenyl] O-ethyl S-n-propyl phosphorodithioate S-[5-(4'-chlorobenzenesulfonyloxy)-2,4-dichlorophenyl] O-ethyl S-n-propyl phosphorodithiote O-ethyl S-n-propyl S-[2,5-dichlorophenyl-4-(p-toluenesulfonyloxy)] phosphorodithioate S-[4-(benzenesulfonyloxy)-2-methylphenyl] O-ethyl S-isobutyl phosphorodithioate S-[3-(benzenesulfonyloxy)-4-chloro-2,6-dimethylphenyl] O-ethyl S-n-propyl phosphorodithioate S-[3-(benzenesulfonyloxy)-2,5-dimethylphenyl] O-ethyl S-n-propyl phosphorodithioate S-[3-(benzenesulfonyloxy)-4-methoxyphenyl] O-methyl S-n-propyl phosphorodithioate O-ethyl S-[4-(1-naphthylmethylenesulfonyloxy)phenyl] S-n-propyl phosphorodithioate O-n-butyl S-[4-(4'-chloro-6'-methyl-2-naphthalenesulfonyloxy)phenyl] S-n-propyl phosphorodithioate S-[4-(5', 7'-dimethyl-2-naphthalenesulfonyloxy)-2-chlorophenyl] O-ethyl S-isobutyl phosphorodithioate O-ethyl O-[4-(1-naphthalenesulfonylthio)phenyl] s-n-propyl phosphorothiolate O-ethyl S-[3-(2-napthalenesulfonyloxy)phenyl] S-n-propyl phosphorodithioate and the like.

The compounds of this invention can be prepared by reacting a phenol or thiophenyl with an O,S-dialkylphosphorochloridothiolate or phosphorochloridodithioate. The general reaction can be represented by the following equation:

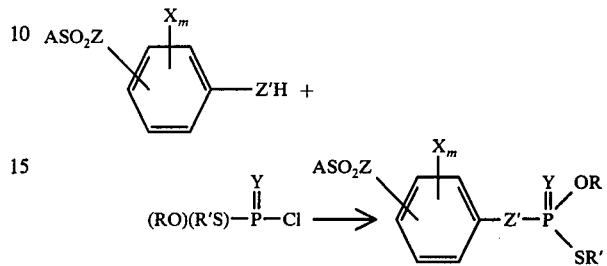

wherein A, R, R', X, Y, Z, Z' and m are as defined for Formula I.

An acid acceptor such as a tertiary amine or an alkali carbonate or hydroxide can be employed as a scavenger in the preparation. Representative acid acceptors include pyridine, trimethylamine, dimethylaniline, lithium carbonate, sodium hydroxide, potassium hydroxide and the like. Generally, a substantially equimolar ratio of reactants is preferred, but an excess of any of the reactants can be employed. While not required, the reaction is advantageously carried out in the presence of an inert organic solvent such as an ether, aromatic hydrocarbon, halogenated aromatic hydrocarbon, aliphatic hydrocarbon, aliphatic ketone, aliphatic nitrile, and the like. Suitable solvents include benzene, toluene, heptane, methylethyl ketone, acetone, ethyl ether, acetonitrile and dioxane. The reaction is generally conducted in a temperature range of about $-10°$ to about $100°$ C. or more, and preferably in the range of about $0°$ to about $60°$ C.

Another method of preparing the compounds of this invention involves reacting an alkali phenoxide or thiophenoxide with an O,S-dialkylphosphorochloridothiolate or phosphorochloridodithioate. The general reaction can be represented by the following equation:

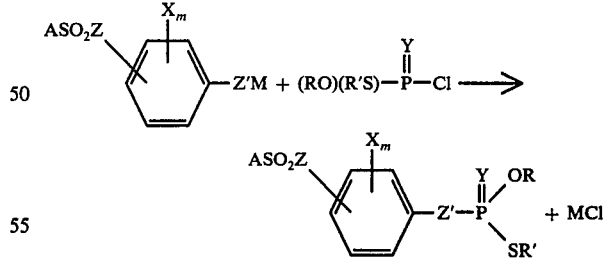

wherein A, R, R', X, Y, Z, Z', and m are as defined for Formula I and M is an alkali metal, such as sodium, potassium or lithium.

Reaction conditions, including choice of solvents, temperature, and molar ratios correspond to the conditions described above for the reaction of an O,S-dialkylphosphorochloridothiolate or phosphorochloridodithioate with a phenol or thiophenol, except that it is not necessary to employ an acid acceptor in this reaction.

In addition, certain compounds of this invention can be prepared by selectively reacting a (di)thiophenol or the S-mono-alkali (di)thiophenoxide with a O,S-dialkyl-phosphorochloridothiolate or phosphorochloridodithioate under reaction conditions described in the procedures above.

The resultant S-[O,S-dialkylphosphorylated] phenol or thiophenyl is then reacted with the appropriate alkyl-, cycloalkyl-, aralkyl- or arylsulfonyl halide using standard procedures.

The general reaction can be represented by the following equation:

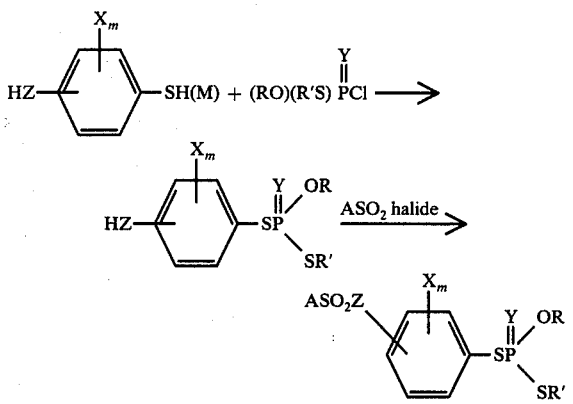

wherein R, R', X, Y, Z, Z' and m are as defined for Formula I, and M is an alkali metal, such as sodium, potassium or lithium.

All of the starting materials used in the preparation of the compounds of this invention are known compounds or are readily prepared by adaptations of known routes. For example, the [alkyl(aryl)sulfonyloxy]thiophenols are prepared by sulfonylation of a suitably S-protected hydroxythiophenol such as S-acetyl p-hydroxythiophenol [F. G. Bordwell and P. J. Bouten, J. Am. Chem. Soc., 78 854 (1956)] and subsequent removal of the S-protecting group by standard means such as hydrolysis, transesterification, etc.

The [alkyl(aryl)sulfonylthio] phenols and thiophenols are prepared by the reaction of a sulfonyl iodide [(R. Otto and J. Troger, Chem. Ber., 24 478 (1891) or L. Field, T. F. Parsons and R. R. Crenshaw, J. Org. Chem., 29 918 (1964)] with a silver mercaptide [D. T. Gibson, C. J. Miller and S. Smiles, J. Chem. Soc., 1821 (1925)].

The O,S-dialkylphosphorochloridothiolates are known in the literature and are prepared by reacting an alkylsulfenylchloride with a dialkyl chlorophosphite [A. F. Lippman, J. Org. Chem., 30, 3217 (1965)].

The following examples are given by way of illustration and are not to be considered as limitations of the present invention. Examples 1 to 4 are illustrative preparations of starting materials useful in the synthesis of compounds of this invention.

EXAMPLE 1

S-(4-(methanesulfonyloxy)phenyl] thioacetate

A solution of 11.5 g. (0.10 mole) of methanesulfonyl chloride in 20 ml. of toluene is added dropwise to a stirring solution of 16.7 g. (0.099 mole) of S-acetyl p-hydroxy thiophenyl in 200 ml. of 3:1 toluene: acetonitrile at 5° C. A solution of 10.1 g. (0.10 mole) of triethylamine in 20 ml. of toluene is then added dropwise to the stirring solution over a period of 30 minutes at 5° C. There is a mild exotherm and triethylamine hydrochloride begins to precipitate out shortly after the addition is completed.

The mixture is held overnight at room temperature and then filtered to remove triethylamine hydrochloride. The filtrate is concentrated in vacuo to give 22.7 g. (93%) of the methanesulfonyloxyphenyl thioacetate as a white crystalline solid, m.p. = 76°–79° C.

EXAMPLE 2

4-(methanesulfonyloxy)thiophenol

S-[4-(methanesulfonyloxy)phenyl] thioacetate (20.4 g., 0.083 mole) is dissolved in 150 ml. of warm (45° C.) methanol. Concentrated hydrochloric acid, 5 ml., is added and the solution is held at 45°–55° C. for 2 hours. The solution is then concentrated in vacuo to approximately 40 ml., taken up in 200 ml. of chloroform, washed with 50 ml. of water, dried over sodium sulfate and concentrated in vacuo to give 15.8 g. (93%) of the desired thiophenol as a white crystalline solid, m.p.=66°–68° C. (after recrystallization from carbon tetrachloride). Analysis calc. (found): C 41.2 (41.3); H 3.95 (4.03).

EXAMPLES 3 and 4

In a manner analogous to that of Examples 1 and 2, the following are prepared:

S-[4-(benzenesulfonyloxy)phenyl] thioacetate Yield: 100% as a pale yellow liquid
4-(benzenesulfonyloxy)thiophenol Yield: 91% as pale yellow oil. Anal. calc. (found) C 54.1 (54.5); H 3.78 (3.87).

EXAMPLE 5

O-ethyl S-[4-(methanesulfonyloxy)phenyl] S-n-propyl phosphorodithioate

A solution of 5.47 g. (0.026 mole) of O-ethyl S-n-propyl phosphorochloridothiolate in 30 ml. of toluene is added dropwise to a stirring solution of 4.30 g. (0.021 mole) of 4-(methanesulfonyloxy)thiophenyl in 100 ml. of toluene at room temperature. The solution is then cooled to 5° C. and held at this temperature while 2.53 g. (0.025 mole) of triethylamine in 40 ml. of toluene is added dropwise over a 30 minute period. There is a mild exotherm and triethylamine hydrochloride begins to precipitate shortly after the addition begins.

The slurry is held at room temperature for an additional hour and then filtered to remove the triethylamine hydrochloride. The filtrate is then concentrated in vacuo to give 7.7 g. (99%) of the phosphorodithioate as a pale yellow oil. Anal.calc. (found): C 38.9 (38.1); H 5.17 (5.44).

EXAMPLE 6

S-[4-(benzenesulfonyloxy)phenyl] O-ethyl S-n-propyl phosphorodithioate

A solution of 5.47 g. (0.026 mole) of O-ethyl S-n-propyl phosphorochloridothioate in 20 ml. of acetonitrile is charged in one portion to a solution of 6.65 g. (0.025 mole) of 4-(benzenesulfonyloxy)thiophenol in 200 ml. of acetonitrile. The solution is stirred and cooled to 4° C. while 2.53 g. (0.025 mole) of triethylamine in 20 ml. of acetonitrile is added dropwise over a 30 minute period. The mixture is held at 5° C. for an additional hour and then concentrated in vacuo. The residue, a mixture of oil and solid, is taken up in 200 ml. of benzene and filtered to remove amine hydrochloride. The filtrate is washed once with 50 ml. of 5% sodium bicarbonate, once with 30 ml. of water, once with 30 ml. of saturated sodium chloride, dried over sodium sulfate, and concentrated in vacuo to give 9.1 g. (84%) of the phosphorodithioate as a pale yellow oil. Anal. calc. (found): C 47.2 (47.3); H 4.8 (5.15).

EXAMPLES 7 to 21

In a manner analogous to that of Examples 5 and 6, the following compounds are likewise readily prepared:

O-ethyl S-[2-(methanesulfonyloxy)phenyl] S-n-propyl phosphorodithioate

S-[3-(benzenesulfonyloxy)phenyl] O-ethyl S-n-propyl phosphorodithioate

O-[4-(benzenesulfonylthio)phenyl] O-ethyl S-n-propyl phosphorothiolate

O-ethyl S-[3-(methanesulfonylthio)phenyl] S-n-propyl phosphorodithioate

S-[4-(chloromethanesulfonyloxy)phenyl] O-ethyl S-n-propyl phosphorodithioate

O-ethyl S-isobutyl S-[4-(methanesulfonyloxy)phenyl] phosphorodithioate

S-sec-butyl O-ethyl S-[4-(methanesulfonyloxy)phenyl] phosphorodithioate

O-ethyl S-[4-(methanesulfonyloxy)phenyl] s-n-propyl phosphorotrithioate

S-[4-(benzenesulfonyloxy)phenyl] O-ethyl S-n-propyl phosphorotrithioate

O-ethyl O-[4-(methanesulfonylthio)phenyl] S-n-propyl phosphorothiolate

S-[4-(4'-chlorobenzenesulfonyloxy)phenyl] O-ethyl S-isobutyl phosphorodithioate

S-sec-butyl O-ethyl S-[4-(p-toluenesulfonyloxy)phenyl] phosphorodithioate

O-methyl S-n-propl S-[4-(α-toluenesulfonyloxy)phenyl] phosphorodithioate

S-n-butyl O-ethyl S-[4-(4'-nitrobenzenesulfonyloxy)-phenyl] phosphorodithioate

The compounds of this invention are useful for the protection of plants and animals, including man, from the ravages of harmful and annoying pests and the disease organisms which they may carry. These compounds are particularly effective against nematodes and arthropods (e.g., acarids and insects) in varying stages of development. As arthropodicides, the compounds of this invention are especially effective against members of the Class Arachnoidea, which includes the Order Acarina, as represented by mites and ticks, and the Class Insecta, the insects. Among the nematodes and arthropods which are effectively controlled by the compounds of the present invention are soil nematodes, e.g. the southern root knot nematode (*Meloidogyne incognita*), the chewing insects, e.g., the southern armyworm (*Spodoptera eridania*), the sucking insects, e.g., the green peach aphid (*Myzus persicae*), soil-dwelling insects, e.g., the southern corn rootworm (*Diabrotica undecimpunctata howardi*), houseflies, (*Musca domestica*), mites, e.g., the two-spotted spider mite (*Tetranychus urticae*), and others.

The compounds of this invention are also active as fungicides, e.g., as phytopathogenic fungicides. Some of the plant fungicidal diseases controlled by compounds of this invention include, for example, bean powdery mildew (*Erysiphe polygoni*), grape downy mildew (*Phasmopora viticola*), rice blast (*Piricularia oryzae*), barley net blotch (*Helminthosporium teres*), gray mold (*Botrytis cinerea*) and the like.

Generally, control of pests is achieved in accordance with this invention by application of the compounds of this invention in pesticidally (i.e., acaricidally, insecticidally, nematocidally, fungicidally) effective amounts either directly to the pests to be controlled or to the loci to be protected from attack by such pests. For example, food, fiber, forage, forest, and ornamental crops and stored products thereof would represent plant protection loci. Treatment with the compounds of this invention of domestic animals, man and their immediate environs similarly constitute representative loci for protection against various annoying ectoparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of any living organism. Such means can comprise a complete killing action, eradication, arresting in growth, repulsion, inhibition, reduction in number, or any combination thereof.

For use as pesticides, the compounds of this invention can be used as solutions, suspensions, or mixtures, in organic solvents or formulations. For example, they can be formulated as wettable powders, emulsifiable concentrates, dusts, granular formulations or flowable emulsifiable concentrates. In such formulations, the compounds of this invention are present at a concentration of about 0. 0001 to about 99%, preferably about 1 to about 95%, and are extended with an agronomically acceptable liquid or solid carrier. When desired, suitable surfactants are likewise incorporated. Surfactants commonly used in the art can be found in the John W. McCutcheon, Inc. publication "Detergents and Emulsifiers Annual."

By "agronomically acceptable carrier" is meant any substance which can be uitilized to dissolve, disperse or diffuse the chemical incorporated therein without impairing the effectiveness of the toxic agent and which does no permanent damage to such environment as soil, equipment, and agronomic crops.

The compounds of this invention can be taken up on or mixed with a finely particled solid carrier, as for example, clays, inorganic silicates, carbonates, and silicas.

Organic carriers can also be employed. Dust concentrates are commonly made wherein compounds are present in the range of about 20 to about 80%. For ultimate applications, these concentrates are normally extended with additional solid to give an active ingredient content of from 1 to about 20%. Granular formulations are made using a granular or pelletized form of carrier, such as granular clays, vermiculite, charcoal or corn cobs, and may contain the active ingredient in from about 1 to about 25% by weight.

Wettable powder formulations are made by incorporating the compounds of this invention in an inert, finely divided solid carrier along with a surfactant which can be one or more emulsifying, wetting, dispersing, or spreading agents or a blend of these. The compounds are usually present in the range of about 10 to about 80% by weight and surfactants in from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the compounds of this invention onto the solid carrier by means of a volatile solvent, such as acetone. In this manner, adjuvants, such as activators, adhesives, plant nutrients, synergists and various surfactants can also be incorporated.

Emulsifiable concentrate formulations are prepared by dissolving the compounds of this invention in an agronomically acceptable organic solvent and adding a solvent soluble emulsifying agent. Suitable solvents are usually water-immiscible can be found in the hydrocarbon, chlorinated hydrocarbon, ketone, ester, alcohol and amide classes of organic solvents. Mixtures of solvents are commonly employed. The surfactants useful as emulsifying agents can constitute about 0.5 to about 10% by weight of emulsifiable concentrates and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. In certain situations, however, it may be desirable and advantageous to apply the compounds directly onto the loci to be protected or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purposes for such application, the compound being utilized, the frequency of dissemination, and the like.

Many of the above formulations can be utilized on animals for the control of parasites.

For use as arthropodicides, e.g., acaricides and insecticides, dilute sprays can be applied at concentrations of about 0.01 to about 20 pounds of the active ingredients per 100 gallons of spray. They are usually applied at about 0.1 to about 5 pounds per 100 gallons. In more concentrated sprays, the active ingredient is increased by a factor of 2 to 40. With dilute sprays, applications are usually made to the plants until run-off is achieved, whereas with more concentrated or low-volume sprays, the materials are applied as mists.

For use as a nematocide or as a soil insecticide, the compounds can be applied as a dilute liquid preparation or as a solid formulation, preferably a granular formulation, by broadcasting, side-dressing, introduction into the seed furrow, soil incorporation, or seed treatment. The application rate can be from about 1 to about 50 pounds per acre of active ingredient and for economic reasons, preferably from about 1 to about 25 pounds per acre.

For use as a fungicide, the compounds of this invention can be applied as fungicidal sprays by methods commonly employed, such as, conventional high-gallonage hydraulic sprays, low-gallonage sprays, air-blast sprays aerial sprays and dusts. The dilution and rate of application will depend upon the type of equipment employed, the method of application and diseases to be controlled, but the preferred effective amount is usually about 0.1 lb. to about 50 lbs. per acre of the active ingredient.

As a fungicidal seed protectant, the amount of toxicant coated on the seed is usually at a dosage rate of about 0.1 to about 20 ounces per hundred pounds of seed. As a soil fungicide the chemical can be incorporated in the soil or applied to the surface usually at a rate of about 0.1 to about 50 lbs. per acre. As a foliar fungicide, the toxicant is usually applied to growing plants at a rate of about 0.25 to about 10 lbs. per acre.

The compounds of this invention can be utilized as the sole pesticidal agents or they can be employed in conjunction with other bactericides, fungicides, herbicides, insecticides, acaricides, and comparable pesticides.

Many variations of this invention are possible without departing from the spirit or scope thereof.

We claim:

1. A compound of the formula:

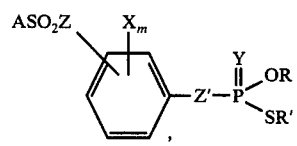

wherein
R is a ($C_1$-$C_4$) alkyl group;
R' is a ($C_3$-$C_6$) alkyl group;
Y is an oxygen or sulfur atom;
Z is an oxygen or sulfur atom;
Z' is an oxygen or sulfur atom, provided that Z and Z' are not simultaneously oxygen atoms;
X is a halogen atom, a ($C_1$-$C_5$) alkyl group, or a ($C_1$-$C_5$) alkoxy group;
m is an integer from 0 to 3; and
A is
a. a ($C_1$-$C_6$) alkyl group optionally substituted with up to three halogen atoms;
b. a ($C_5$-$C_6$) cycloalkyl group;
c. a ($C_7$-$C_{11}$) aralkyl group, the aryl portion of which is optionally substituted with up to three substituents selected from the group consisting of halogen, nitro, ($C_1$-$C_5$) alkyl and ($C_1$-$C_5$) alkoxy; or
d. an aryl group of the formula:

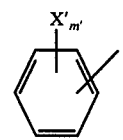

or

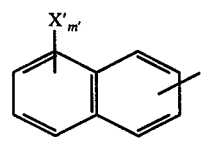

wherein

X' is a nitro group, a halogen atom, a ($C_1$-$C_5$) alkyl group, or a ($C_1$-$C_5$) alkoxy group; and m' is an integer from 0 to 3.

2. A compound according to claim 1 wherein R' is a ($C_3$-$C_5$) alkyl group of the formula:

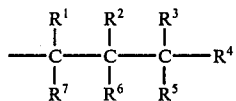

wherein $R^1$-$R^7$ are individually hydrogen, methyl, or ethyl.

3. A compound according to claim 2 wherein Y is an oxygen atom.

4. A compound according to claim 3 wherein Z is an oxygen atom and Z' is a sulfur atom.

5. A compound according to claim 4 having the formula:

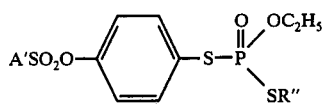

wherein

R" is a n-propyl, isobutyl, or sec-butyl group; and

A' is a ($C_1$-$C_5$) alkyl group or a phenyl group optionally substituted with up to three substituents selected from the group consisting of methyl, nitro and chloro.

6. A compound according to claim 5 having the formula:

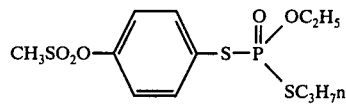

7. A compound according to claim 5 having the formula:

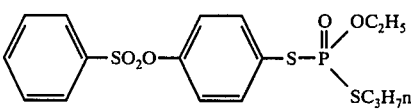

8. A pesticidal composition comprising a pesticidally effective amount of a compound according to claim 1 and an agronomically acceptable carrier.

9. A pesticidal composition comprising a pesticidally effective amount of a compound according to claim 5 and an agronomically acceptable carrier.

10. A method of controlling pests which comprises applying directly to the pests or to the loci to be freed of or protected from attack by such pests, a pesticidally effective amount of a compound of claim 1.

11. A method of controlling pests which comprises applying directly to the pests or to the loci to be freed of or protected from attack by such pests, a pesticidally effective amount of a composition of claim 8.

12. A method according to claim 11 wherein the pests are phytopathogenic fungi.

13. A method according to claim 11 wherein the pests are acarids.

14. A method according to claim 11 wherein the pests are nematodes.

15. A method according to claim 11 wherein the pests are insects.

* * * * *